United States Patent [19]
Stewart et al.

[11] Patent Number: 6,053,171
[45] Date of Patent: Apr. 25, 2000

[54] PLASMA TREATED TUBING

[75] Inventors: Mark T. Stewart, Lino Lakes;
Kenneth E. Cobian, St. Anthony;
Michael J. Ebert, Fridley, all of Minn.

[73] Assignee: Medtronic, Inc., Minneapolis, Minn.

[21] Appl. No.: 09/262,625

[22] Filed: Mar. 4, 1999

Related U.S. Application Data

[62] Division of application No. 08/923,046, Sep. 3, 1997.

[51] Int. Cl.$^7$ .................................................... A61B 19/00
[52] U.S. Cl. .......................................................... 128/897
[58] Field of Search .................................. 128/697, 699;
604/205

[56] References Cited

U.S. PATENT DOCUMENTS

| | | | |
|---|---|---|---|
| 4,261,806 | 4/1981 | Asai et al. ................................ | 204/165 |
| 4,488,954 | 12/1984 | Hatada et al. ........................... | 204/169 |
| 4,508,606 | 4/1985 | Andrade et al. ......................... | 204/169 |
| 4,752,426 | 6/1988 | Cho .......................................... | 264/22 |
| 5,080,924 | 1/1992 | Kamel et al. ............................. | 427/2 |
| 5,133,422 | 7/1992 | Coury et al. ............................. | 128/784 |
| 5,244,654 | 9/1993 | Narayanan ............................ | 424/78.17 |
| 5,476,501 | 12/1995 | Stewart et al. ........................... | 607/127 |
| 5,486,357 | 1/1996 | Narayanan ............................ | 424/78.17 |
| 5,593,550 | 1/1997 | Stewart et al. ........................... | 204/165 |
| 5,597,456 | 1/1997 | Maruyama et al. ..................... | 204/165 |

FOREIGN PATENT DOCUMENTS

| | | |
|---|---|---|
| 0 348690 A2 | 1/1990 | European Pat. Off. . |
| 0 496 305 A2 | 7/1992 | European Pat. Off. . |
| 0 665 304 A1 | 8/1995 | European Pat. Off. . |
| WO 95/20688 | 8/1995 | WIPO . |

OTHER PUBLICATIONS

C. Karl, "Hydromer Coatings For Medical Devices", Brochure from *Hyrdomer, Inc*, Whitehouse, NJ, p. 1–4 (Undated).

N. Nurdin et al., "Reduced Frictional Resistance of Polyurethane Catheter by Means of a Surface Coating Procedure", *Journal of Applied Polymer Science*, 61, p. 1939–1948 (1996).

*Primary Examiner*—William E. Kamm
*Attorney, Agent, or Firm*—Thomas F. Woods; Harold R. Patton

[57] ABSTRACT

Polymeric tubing having an outer surface with a reduced coefficient of friction. The outer surface is treated by an exposure to a plasma glow discharge in the presence of an inert gas, and by deposition of a monomer during exposure to the plasma glow discharge for a time sufficient to modify the slip characteristics of the surface of the tube. The tube is preferably exposed to plasma glow discharge for a time sufficient to reduce the coefficient of friction by at least 70%. The tubing may be fabricated of silicone rubber, and the monomer deposited may be N-vinyl-2-pyrrolidone.

6 Claims, 11 Drawing Sheets

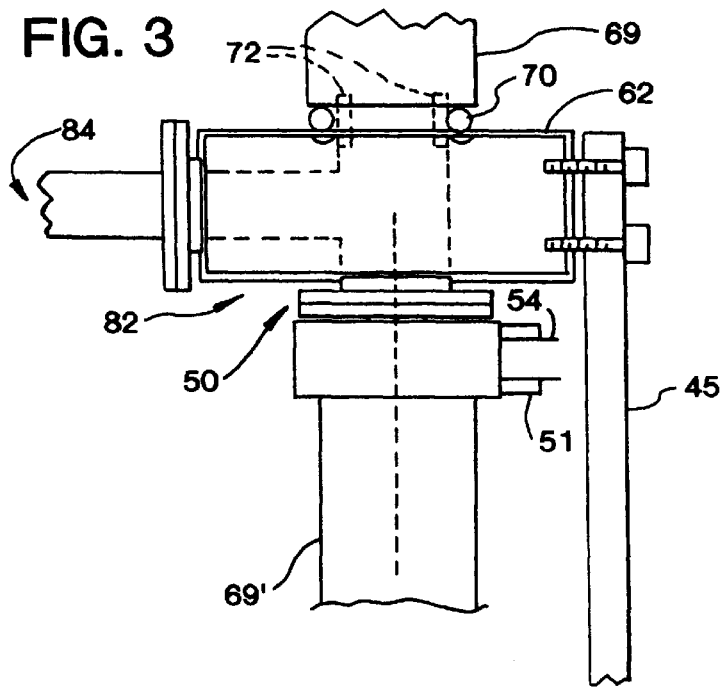
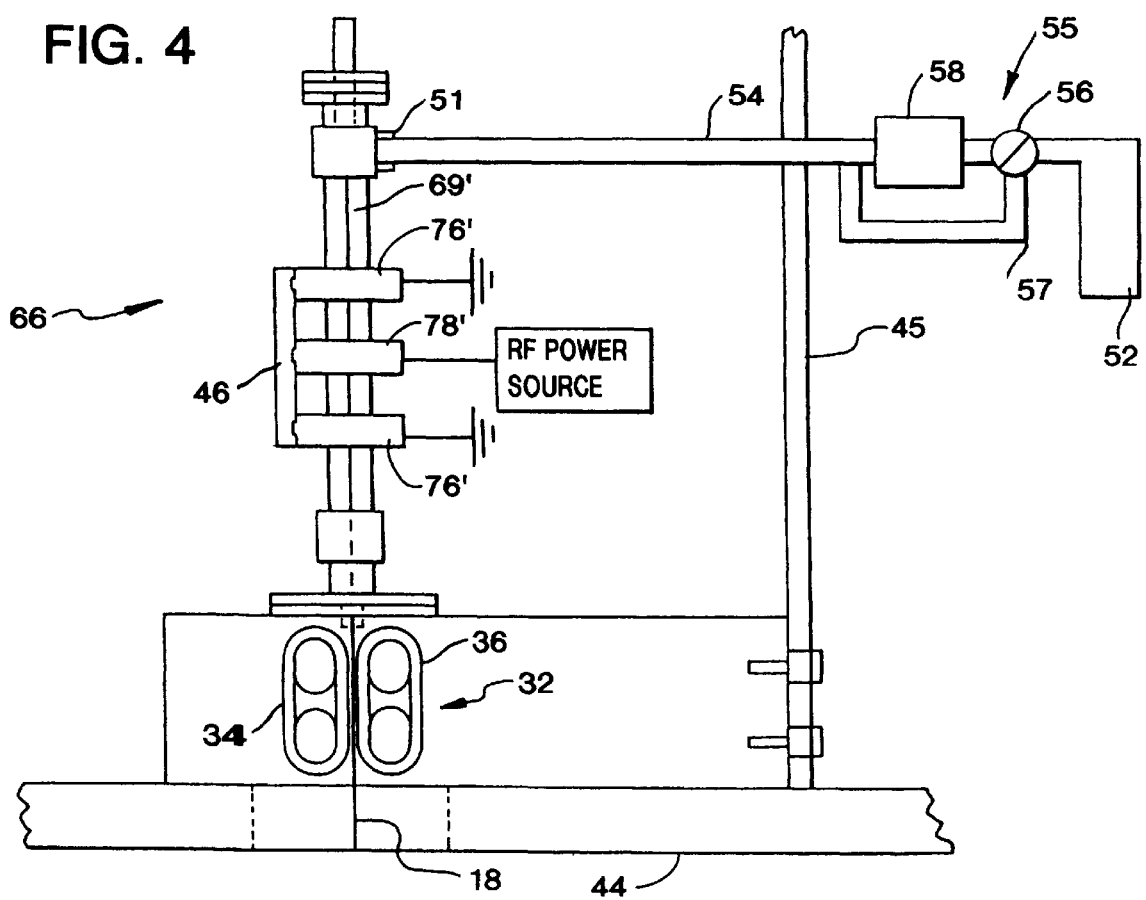

PLASMA TREATED TUBING

This application is a divisional application of U.S. patent appln. Ser. No. 08/923,046 filed Sep. 3, 1997 entitled "Plasma Process for Reducing Friction on Polymeric Surfaces" to Stewart et al.

BACKGROUND OF THE INVENTION

This invention relates to surface modification of the slip characteristics of polymeric surfaces. In particular, surfaces of tubing composed of polymeric materials such a silicone rubber, polypropylene, polyethylene, polyvinylchloride, fluoropolymers and the like or other dielectric materials and to improved methods and apparatuses for effecting such modifications.

Polymeric plastic tubing, particularly that of small diameter, and most especially that of silicone rubber, is used in many medical applications and devices. In particular, silicone rubber (especially cross linked silicone elastomer with silica filling) is the polymer of choice for tubing in many medical applications involving implantation.

Catheters prepared from polymeric materials are used frequently in such routine procedures as the delivery of intravenous fluids, removal of urine from compromised patients, chemical sensing using a variety of chemical transducers, monitoring cardiovascular dynamics, and treating cardiac and vascular disorders. Catheters provide the pathway to previously inaccessible body areas for both diagnostic and therapeutic procedures, thereby reducing the need for surgery. For example, double catheter systems are utilized for drug delivery or occlusion of blood flow to specific organs or tissues. Typically, a rigid outer catheter and a buoyant, flexible inner catheter that can freely float in the blood stream are used in such procedures. Another example is a pacing lead which utilizes a small diameter tubing such as less than 0.055 inch (1.40 mm) (OD) with an inner diameter (ID) of 0.35 inch (0.9 mm). In this type of lead, an elongate wire core (usually in the form of a coil) having a helical screw-in electrode at its distal end is placed inside the small diameter tubing to provide a catheter-like device. The core wire is manipulated at the proximal end of this arrangement by the physician during implantation to screw the helical electrode into heart tissue and fix the lead in place. Of course these catheter-like devices may involve other structures not described herein for simplicity.

As catheterization techniques have become more complicated, more demands placed on the performance of the catheter have increased. For instance, the paths that these catheters must take through the body are often long and tortuous, such as accessing the cranial vessels via the femoral artery. The polymeric materials from which catheters are made, such as silicone rubber, have a tacky surface upon exposure to an aqueous environment. This causes excessive friction, making placement of the catheter-like device in the body difficult. Further, these friction characteristics also make torque transfer through the tubing difficult thus, for example, making difficult the turning of the core wire which is preferably a torsion coil in the aforementioned "screw in" pacing lead to screw the helical electrode into tissue.

Previous practices to ameliorate these friction characteristics have involved: 1) the use of harder materials which are more slippery but less biostable and less suitable for implantation, e.g., polyurethane; 2) coating; 3) hardening; 4) swelling; and even 5) the use of environmentally unfriendly materials such as chlorofluorocarbons (CFC). For example, polyurethane catheters have been coated with a composition of a poly(vinyl pyrrolidone) (PVP) crosslinked with an isocyanate (commercially available under the trade designation "HYDROMER" from Hydromer Inc., New Jersey). See, e.g., "Reduced Frictional Resistance of Polyurethane Catheter by Means of a Surface Coating Procedure," by Nurdin, N., et al., *Journal of Applied Polymer Science*, Vol. 61, 1939–1948 (1996), herein incorporated by reference.

Plasma discharge has also been used on tubing with some degree of success. More specifically, exposure of polymeric surfaces to plasma discharge is effective in modifying the surface to improve its slip characteristics. For example, U.S. Pat. No. 5,593,550 (Stewart et al.) is directed to a plasma process for improving the slip characteristics of polymeric tubing on its OD and ID. U.S. Pat. No. 5,133,422 (Coury et al.) is directed to improving the slip characteristics of polymeric tubing on its OD by plasma treatment in the presence of a gas selected from the group consisting of hydrogen, nitrogen, ammonia, oxygen, carbon dioxide, $C_2F_6$, $C_2F_4$, $C_3F_6$, $C_2H_4C_2H_2$, $CH_4$, and mixtures thereof. U.S. Pat. No. 4,692,347 (Yasuda) is directed to plasma deposition of coatings and to improving blood compatibility on both the OD and the ID surfaces of polymeric tubing by coating it under discharge conditions in a single chamber.

The theory and practice of radio frequency (RF) gas discharge is explained in detail in 1) "Gas-Discharge Techniques For Biomaterial Modifications" by Gombatz and Hoffman, *CRC Critical Reviews in Biocompatibility*, Vol. 4, Issue 1 (1987) pp 1–42; 2) "Surface Modification and Evaluation of Some Commonly Used Catheter Materials I Surface Properties" by Triolo and Andrade, *Journal of Biomedical Materials Research*, Vol. 17, 129–147 (1983), and 3) "Surface Modification and Evaluation of Some Commonly Used Catheter Materials, II. Friction Characterized" also by Triolo and Andrade, *Journal of Biomedical Materials Research*, Vol. 17, 149–165 (1983). All of the foregoing are incorporated herein by reference.

A number of patents have been reviewed in which plasma reactors are disclosed which use wave energy (RF or microwave) to excite plasma. Although not admitted as prior art, examples of plasma reactors and methods using the same can be found in the issued U.S. patents listed in Table 1 below.

| LIST OF U.S. PATENTS | | |
|---|---|---|
| U.S. Pat. No. 5,593,550 | 01/14/1997 | Stewart et al. |
| U.S. Pat. No. 5,244,654 | 09/14/1993 | Narayanan |
| U.S. Pat. No. 5,223,308 | 06/29/1993 | Doehler |
| U.S. Pat. No. 5,133,986 | 07/28/1992 | Blum et al. |
| U.S. Pat. No. 5,133,422 | 07/28/1992 | Coury et al. |
| U.S. Pat. No. 4,948,628 | 08/14/1990 | Montgomery et al. |
| U.S. Pat. No. 4,927,676 | 05/22/1990 | Williams et al. |
| U.S. Pat. No. 4,846,101 | 07/11/1989 | Montgomery et al. |
| U.S. Pat. No. 4,752,426 | 06/21/1988 | Cho |
| U.S. Pat. No. 4,718,907 | 01/12/1988 | Karwoski et al. |
| U.S. Pat. No. 4,692,347 | 09/08/1987 | Yasuda |
| U.S. Pat. No. 4,448,954 | 12/18/1984 | Hatada et al. |
| U.S. Pat. No. 4,261,806 | 04/14/1981 | Asai et al. |

It is a primary object of this invention to provide polymeric surfaces which exhibits improved slip characteristics. This and other objects will be clear from the following description.

SUMMARY OF THE INVENTION

Although this invention is applicable to surfaces of polymeric materials and dielectric materials, it will be described herein with particular reference to silicone rubber tubing, one preferred embodiment of the invention. It has been discovered according to this invention that glow discharge coupled with monomer deposition can make a surface of polymeric tubing more lubricious. Preferably, polymeric tubing is placed within a glass reactor or other glow discharge chamber (preferably thick walled glass or a suitable ceramic) which receives the tubing longitudinally. The glow discharge electrodes are applied to the glass reactor or discharge chamber with the plasma discharge gas being inside the glass reactor. The tubing is next passed within a second glass reactor similar to that described above except that a monomer is discharged in the glass reactor. Generally, any electrically non-conductive dielectric reactor chamber means which holds a vacuum will suffice as a discharge chamber. It can be applied to any polymeric surface, such as tubing of any size diameter.

The absolute size of the space relationship between the OD of the polymer tubing and the ID of the glass tube (i.e., "reactor" or "discharge chamber") or other chamber in any given instance will depend on many variables e.g., gas pressure, power applied, relative size of space in the glass tube and the size of the polymeric tubing, and so forth.

For example, the following treatment conditions have provided tubing with a desirable outer surface with respect to its improved slippery characteristics: OD of glass tube is about 0.5" to about 1.5"; the length of the glass tube from about 3" to about 18"; RF power between 300 watts and 30 watts that can be continuous or pulsed power mode, such as about 1 millisecond to about 10 milliseconds; and gas pressure in the plasma reactor of about 0.010 Torr to about 10.0 Torr. The use of pulsed power is an important factor in practicing this invention so that a portion of the monomer is activated to initiate polymerization without substantially adversely affecting pendant functional groups on the monomer.

In any given instance, it can be readily determined empirically by varying discharge conditions and time of exposure to discharge as to what treatment results are obtained and adjusting the conditions to obtain the desired result.

For purposes of this invention, the gas discharge process or radio frequency discharge as contemplated herein need only be such as to give rise to a plasma glow discharge which interacts with surfaces exposed thereto, such as silicone rubber, to alter same by reaction therewith. The plasma discharge apparatus will include a glow discharge chamber or reactor as aforementioned including electric reactor for connection to a radio frequency power source or the like for reactance coupling upon application of power from the source. Also included is a monomer deposition chamber or monomer reactor for exposing the polymer tubing to a zone in which a monomer is deposited on the surface of the polymer tubing. As in the glow discharge chamber, the monomer deposition chamber includes electric reactor for connection to a radio frequency power source or the like for activation of the monomer upon application of power and exposure to a monomer vapor from a monomer source.

The reactor apparatus of the invention and the method thereof overcomes problems of the designs described in the patent literature as follows:

Tubing Length Limitation: The present apparatus can treat the OD surface of virtually unlimited lengths of tubing. The only limitation is how large a spool can be fitted inside of the vacuum chamber. A typical reactor will have a capacity of 1,000 to about 5,000 feet depending on tubing diameter.

Control of Deposition Chemistry: Short pulses of high power, such as about 10 watts to about 300 watts for about 1 to about 10 milliseconds, interrupted by longer "off" periods (about 4 to about 800 milliseconds) provide enough energy to activate the monomer yet limit its overall intensity so that pendant functional groups on the monomer are not significantly adversely altered during deposition. Thus, the use of pulsed power is critical to the success of the method because activation of the monomer is desired without substantially altering the chemical and/or physical characteristics of the monomer during deposition. Accordingly, the present invention relates to the deposition of a monomer to glow discharge pre-treated tubing.

Treatment of Both Outer and Inner Surfaces: In one embodiment, an apparatus and method of the invention utilizes three separate zones in which to first pre-treat the outside of the tubing, treat the inside surface of the tubing and then deposit the monomer on the pre-treated outside surface of the tubing. This is important when treating very small tubing. The small tubing requires a very close fit inside of the ID treatment zone tube to prevent a discharge between tubing and glass as is described in U.S. Pat. No. 4,448,954. This can lead to problems with the tubing sticking inside of the glass tube reactor. However, in the present reactor and method the OD plasma pre-treatment is preferably performed on the tubing prior to its entry into the ID zone for treatment which aides in reducing the friction between the outside of the tubing and reactor to prevent sticking.

Tubing Manageability: Applicants have recognized that providing a lubricious surface on tubing or a catheter should be balanced with the ability of the physician or technician to handle the device during a procedure. For example, it has been reported that certain surface treatments and/or coatings cause the tubing or catheter to become very slimy and slippery when wet. Thus, the physician may have difficulty guiding the catheter to the desired internal location or suturing a lead body to surrounding tissue, for example. Additionally, a portion of the coating may desorb from the surface of the catheter on to the physician's gloves during the procedure which, again, may adversely affect the physician's control of the device. The present invention is directed to the attachment of the monomer to, preferably, the OD surface so that it is stable during manipulation, i.e., plasma polymerized (abbreviated herein as "pp") monomer is less likely to desorb from the tubing surface.

Polymer Surface Dynamics: One of the difficulties in modifying polymer surfaces relates to the mobile nature of amorphous polymer molecules. If a modification, such as oxidation, of a surface is performed, molecular motions can, over a period of time, cause the modified surface to intermingle and diffuse into the polymer matrix. This tendency is most pronounced in silicone elastomers which have very mobile polymer chains. To overcome this problem, plasma treatments may be used to crosslink and stabilize the polymeric surface. However, within hours or even minutes after plasma treatment, the surface begins to revert back to its original hydrophobic state. Uncrosslinked oligomers and low molecular weight oils begin to bloom to the polymeric surface. These oils tend to interfere with attachment or grafting of coatings to the polymer surface. A particularly preferred way to overcome this time dependent phenomenon is to inert gas plasma treat the polymeric surface immediately followed by a modification step, preferably deposition of a suitable monomer, before the polymeric surface begins to revert. In so doing, a polymeric surface can be modified to a relatively long lasting hydrophilic surface.

Other improved properties resulting from coatings and treatments according to the invention are:

reduced permeability to fluids and gases;

reduced "cold flow" of silicone surfaces;

provision of specific surface chemistries by selection of functional coatings; and bondability with adhesives and molding compounds.

BRIEF DESCRIPTION OF THE FIGURES

FIG. 3 is a detailed showing of the transition zone between the plasma pre-treatment and the monomer deposition zones of the apparatus of FIG. 1; and FIG. 4 is a detailed showing of the monomer deposition zone of the apparatus of FIG. 3;

DETAILED DESCRIPTION OF PREFERRED EMBODIMENTS

The invention provides a plasma reactor apparatus and method which produces an improved slip characteristic of polymeric surfaces such as an outer diameter (OD) surface of a polymeric tubing, such as silicone tubing. Improved slip characteristic refers to lower friction upon exposure of tubing treated in accordance with the invention to an aqueous environment when compared to untreated tubing. The treatment has been demonstrated to uniformly improve, increase the lubricity of, the surface of the tubing. It is believed that the method of the invention causes increased bonding of a monomer to the polymeric surface of the tubing, such as by covalent attachment.

The method of the invention is preferably performed continuously meaning that tubing is fed from a spool of 1,000+ feet of tubing and treated, in one preferred embodiment, as it moves through an inert gas plasma glow discharge pre-treatment zone and then a monomer deposition zone of the reactor apparatus after which it passes into a receiving chamber. The plasma glow discharge pre-treatment and the monomer deposition zones each includes a set of radio frequency electrodes or a microwave cavity. In the pre-treatment zone of the apparatus, preferably located just prior to the monomer deposition zone, the outside of the silicone tubing is preferably glow discharge treated to prepare the OD surface of the tubing for monomer deposition in a subsequent zone. This outer pre-treatment zone may include a 0.5 inch or larger glass tube around which is a set of radio frequency electrodes, a coil or a microwave cavity used to excite a glow discharge around the outside of the plastic tubing.

The glow discharge pre-treatment of the outside of the polymeric tubing described above may involve the use of "inert" gases, i.e., gases that will not polymerize under plasma discharge conditions as set forth herein. Preferably, inert gases are selected from the group of helium, neon, argon, nitrogen, and combinations thereof. Combinations of the inert gases can also be beneficial to make the initiation of the discharge easier. The polymeric tubing is filled with gas to a stable pressure while the pre-treatment zone is maintained at a relatively lower pressure which is usually more desirable for the outer surface plasma treatment. Pressure differentials are not critical but can be desirable. These differential pressures are maintained by using gas flow controls, orifices, and automatic exhaust valve pressure controllers (not shown in any detail).

In another sense, this invention provides tubing having modified slip characteristics on the inside surfaces thereof particularly small diameter silicone tubing of less than about 1 mm in OD. This is accomplished by means of plasma discharge within the tubing. Improved apparatus for accomplishing this is also provided.

Figure 1:
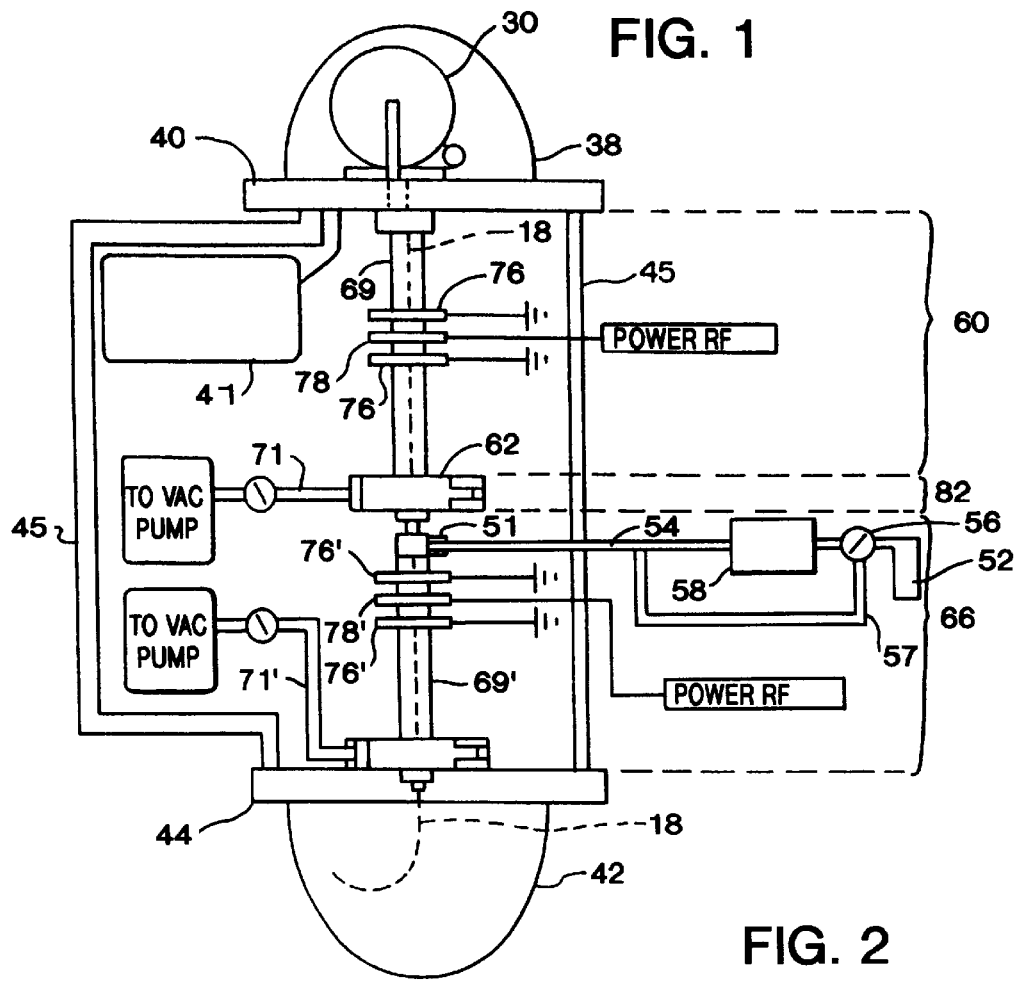
FIG. 1 is a showing of an apparatus according to the invention for plasma discharge pre-treating and depositing a monomer on an OD surface on a continuous basis.

In FIG. 1, the pre-treatment zone 60 is the first plasma that the tubing 18 passes through after coming off of reel 30. The top of this section of the apparatus seals against the underside of the top plate assembly 40. The bottom of this section seals against the "transition zone" block 62. In the pre-treatment zone 60, the tubing 18 receives an inert gas plasma pre-treatment on its outer surface.

Figure 2:
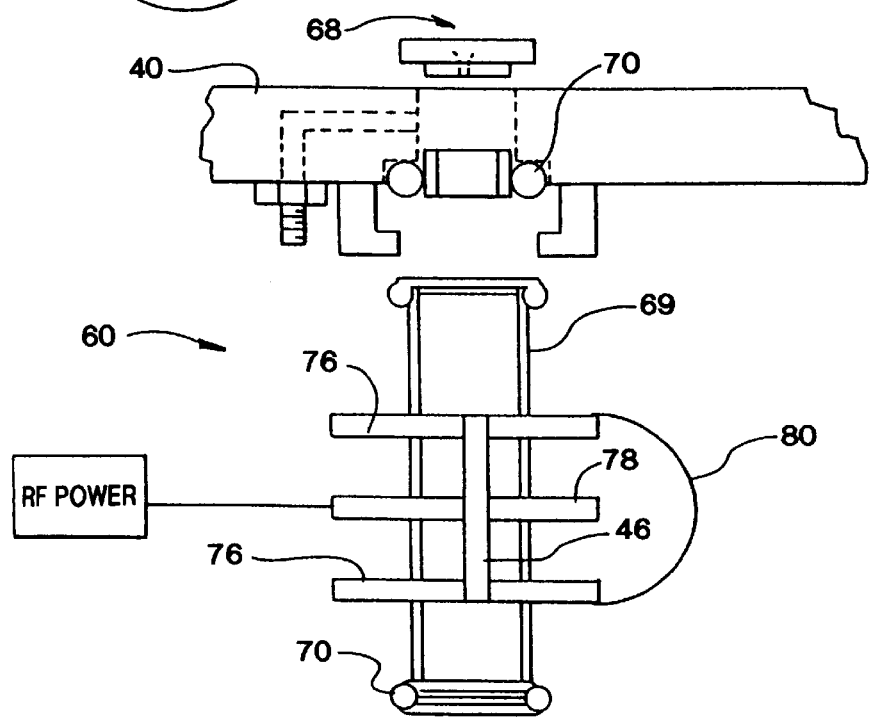
FIG. 2 is a detailed showing of the OD pre-treatment zone of the apparatus of FIG. 1.

Upon entry into pre-treatment or glow discharge zone 60, the tubing may pass through a close fitting orifice 68, best seen in FIG. 2, which generally should have a diameter equal to the tubing nominal OD plus 0.001 in ±0.001 in. This diameter may vary depending on the type of tubing and type of treatment or coating to be performed. For tubing 0.054" OD the orifice should be drilled to about 0.055". This size may later be adjusted to achieve precise pressure differentials. The orifice serves to a) prevent the glow discharge from spreading into the upper tubing reel chamber 38, b) allow different pressures or types of gasses to be maintained in the upper chamber 38 and pre-treatment zone 60, c) guide the tubing 18 down the center of the pre-treatment zone 60, and d) allow a small gas flow from the upper chamber 38 to the glass tube 69 below where a vacuum exhaust line 71 may be arranged to carry away the flow.

The pre-treatment zone 60 typically includes a section of glass tube 69 which is commonly available as a sanitary glass tube. The length of the glass tube 69 may typically be from about 3 to about 18 inches in length, more preferably from about 6 to about 12 inches in length, and most preferably from about 6 to about 10 inches in length. The glass tube 69 should be capable of forming a vacuum seal with each end of the tube butting up against a O-ring 70, see FIG. 2. Provision is made to allow for entry of gases below the orifice 68 and above the end of the glass tube 69.

Preferably, the glass tube 69 has a diameter sufficiently large so that the pre-treatment of the OD surface is substantially uniform. More preferably, the diameter is about 0.5" to about 1.5" and most preferably, about 1.5". When the OD of the glass tube 69 is less than about 0.5", the tubing 18 must be substantially centered in order to maintain a uniform glow discharge at lower gas pressures. Thus, a larger glass tube 69 tolerates more misalignment and provides a more uniform discharge around the tubing 18.

A plurality of circular disc or torus shaped electrodes, shown as 76 and 78 in FIG. 2, are dimensioned to suit the diameter and length of the glass tube 69. A PTFE insulator support bar 46 may be included as shown in FIG. 2. The two ground electrodes 76 may be connected by a common ground strap 80, also shown in FIG. 2.

As the tubing 18 passes through the pre-treatment zone 60, a glow discharge is produced by the inert gas, as defined above, by reactance coupling utilizing power provided by the radio frequency power source, shown as electrodes 76 and 78. Under plasma discharge conditions, the inert gas treatment stabilizes the polymeric surface of the tubing in preparation for application of the monomer. While not wishing to be bound by any particular theory, it is believed that pre-treatment by inert gas plasma causes the polymeric surface of the tubing 18 to crosslink and form a population of free radical sites.

Transition Zone, zone 82—see FIG. 3 in particular, serves as a connection between the pre-treatment zone 60 and the monomer deposition zone 66. Preferably, the transition zone 82 should a) be capable of forming a vacuum seal with the lower end to the pre-treatment glass tube 69, b) connect with the compression fitting 50 of the monomer deposition zone 66 below it, c) provide a vacuum port 84 which connects to an automatic throttle valve pressure controller (this allows gas flow which enters through or below the orifice 68 at the top of the pre-treatment zone 60 to be drawn off below the pre-treatment zone), and d) provide a rigid connection to the upper end of the monomer deposition zone 66 in order to minimize or prevent any relative motion between the top and bottom compression fittings 50 of the monomer deposition zone 66.

The Monomer Deposition Zone 66 (see FIG. 4 in particular) performs the monomer deposition on the OD surface of the tubing 18 as it moves through the deposition zone 66. In the monomer deposition zone 66, a monomer is delivered as a vapor to a very low energy glow discharge zone. Preferably the monomer deposition zone 66 includes an electrode and glass tube configuration similar to that shown in FIG. 2. The pre-treatment on the outer surface tubing 18 in the pre-treatment zone 60 is preferably performed prior to entry into the glass tube 69'.

More importantly, it was found that the plasma pre-treatment of the tubing was critical to obtaining a stable wettable surface after deposition of the monomer. For example, it was found that when the plasma pre-treatment was not uniform around the surface of the tubing, improved slip characteristics were only observed on that portion of the tubing surface that was pretreated.

It was also found that when fully treated tubing was rinsed and soaked overnight in deionized water at room temperature, the tubing was observed to retain a wettable surface. This indicated that the monomer deposition was retained and it is believed that the monomer is bound to the tubing surface. This has been shown by means of IR spectra (FTIR) and friction analysis.

The length of the glass tube 69' is preferably about 6 inches to about 12 inches if using capacitive electrodes. Also, if a helical resonator plasma excitation (13.56 Mhz) source is used, a tube length of close to 18 inches may be required.

Electrode configuration may vary. However, the circular disc or torus shaped electrodes 76' and 78' are dimensioned to suit the diameter and length of the OD tube 69', as described with respect to the pre-treatment zone 60. Also, a PTFE insulator support bar 46 may be included as shown in FIG. 4. The two ground electrodes 76 may be connected by a common ground strap 80 also as shown in FIG. 4. In other words, the configuration may be similar to that in the pre-treatment zone 60, described above.

In addition to an electrode configuration and a glass tube, the monomer deposition zone 66 further includes a monomer source 55, as shown in FIG. 4. The monomer source 55 typically includes a monomer reservoir 52, a mass flow controller 58, a monomer conduit 54 and a monomer inlet 51.

Preferably, a monomer, typically liquid or gas, is held in the monomer reservoir 52. Suitable monomers for use in the present invention includes a compound comprising a polymerizable structure selected from the group of a carbon-carbon double or triple bond, a saturated cyclic group, an arylene group, and mixtures thereof; and one or more pendant functional groups selected from the group of an amine, a hydroxyl, a carbonyl, a carboxylic, an amide, a sulfone, an ether, an ester, an epoxide, and mixtures thereof. A particularly preferred monomer is N-vinyl-2-pyrrolidone (NVP).

The monomer is discharged through the monomer conduit 54 to the monomer inlet 51, where the monomer enters the glass tube 69' of the monomer deposition zone 66. Preferably, the monomer conduit 54 is heated to a temperature approximately equal to or greater than the boiling point of the monomer so that the monomer can be introduced in the monomer deposition chamber 66 without condensation as a monomer vapor. For example, when the monomer is N-vinyl-2-pyrrolidone, the monomer conduit 54 is at a temperature of about 80° C. or greater.

The monomer source 55 may optionally include a by-pass valve 56 around the monomer mass flow controller 58 for removal of monomer reservoir headspace gases prior to the flow of the monomer vapor through the monomer mass flow controller.

Accordingly, for example, it is desirable to provide a flow of NVP vapor to a low energy glow discharge, e.g., about 0.1 to about 100 sccm. While not wishing to be bound by any particular theory, it is believed that by providing low radio frequency power to the monomer deposition zone 66, the discharge primarily activates only the vinyl groups on the NVP monomer, i.e., mildly activating and initiating polymerization of the monomer. Further, it is believed that the mild activation of the monomer in combination with the free radical sites on the polymeric surface of the tubing 18 produced in the pre-treatment zone 60 allows the polymerization of the monomer to proceed without significant alteration of the monomer structure. It is believed that conventional plasma depositions utilize greater energy in the deposition plasma in order to sufficiently activate and stabilize the polymeric surface, i.e., so that the monomer would adhere to the polymeric surface. It is further believed that conventional plasma depositions cause the monomer to retain few chemical and physical properties due to molecular fragmentation that occurs at high energy plasma.

Figure 5:
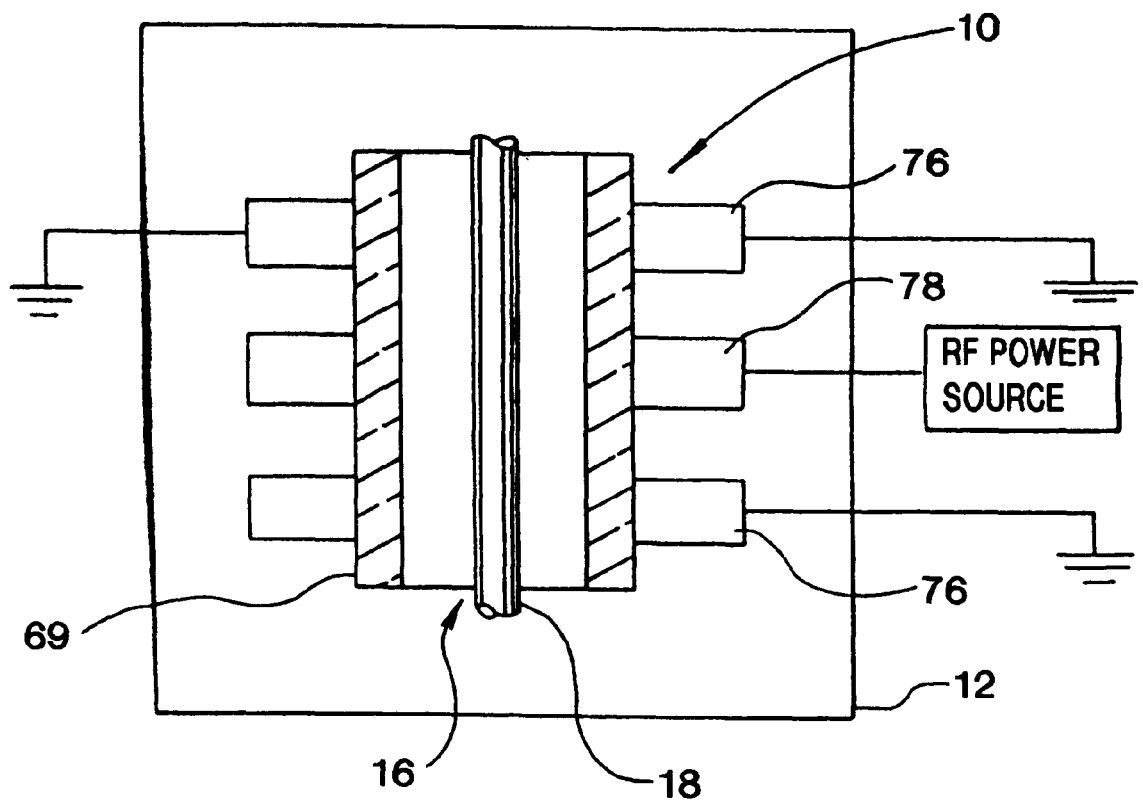
FIG. 5 is a typical schematic arrangement showing how a piece of polymeric tubing is held in a reactor for plasma discharge.

Reference to FIG. 5 schematically shows a preferred configuration of the electrodes and glass tubing for plasma discharge according to one embodiment of the invention. In general, the configuration is useful in the pre-treatment zone 60 and the monomer deposition zone 66 (except where noted). A plasma discharge apparatus generally indicated at 10 is enclosed within an evacuated environment 12. In the pre-treatment zone 60, the evacuated environment 12 may contain an inert gas, preferably an inert gas selected from the group of nitrogen, helium, neon, argon, and mixtures thereof. More preferably, the gas is argon. The gas is at a suitable pressure for discharge such as 0.6 torr. In the monomer deposition zone 66, the evacuated environment 12 may contain the monomer. It was found that the coefficient of sliding friction between the outer diameter surface of a silicone tube and metal can be reduced by about 70% or more with the treatment of the present invention.

The discharge apparatus 10 of FIG. 1 includes a glass reactor and holder tube 69 having a bore 16 therethrough, that is useful in both the pre-treatment zone 60 and the monomer deposition zone 66. Also useful in both zones is a plurality of circular, torus shaped ground electrodes 76, preferably two, and an RF powered electrode 78 that encircle glass tube 69, as shown.

In the pre-treatment zone 60, the RF powered electrode 78 is preferably operated in a continuous mode. For example, it has been found that a power level of about 20 watts to about 300 watts at a continuous mode was effective to pre-treat the tubing so as to permit a substantially uniform deposition of the monomer. In the monomer deposition zone 66, the RF power electrode 78' is preferably operated in a pulse mode. For example, it has been found that pulsing between about 100 watts and about 0 watts for about 2 milliseconds to about 20 milliseconds produced an effective monomer discharge. More preferably, the pulsed power source provides a continuous sequence of "on" periods and "off" periods, where the "on" periods having a duration of about 1 to about 3 milliseconds and the "off" periods have a duration of about 4 to about 20 milliseconds.

In an arrangement such as that shown in FIG. 5, if the length of the tubing 18 is greater than the length of the discharge zone between the electrodes 76 and 78, it will be desirable to make provisions to provide discharge throughout the entire length of the tubing. This may be accomplished in a variety of ways. For example, additional sets of electrodes can be distributed over the length of the apparatus. Also, an arrangement may be provided (not shown) in which the set of electrodes move over the length of the apparatus. Most preferably, the arrangement will be modified to allow the tubing 18 to move through the bore 16 as by being pulled therethrough thus passing the tubing through the discharge zone which exists between the electrodes. An embodiment of this latter preferred arrangement, including both the pre-treatment zone 60 and the monomer deposition zone 66, is shown schematically in FIG. 2. Continuous tension is preferred to avoid having the polymeric tube stick in the reactor.

The apparatus of FIG. 1 shows the tubing 18 held on a reel 30 at the top (or inlet end) of the apparatus from which it is pulled by a means such as a tubing transport track drive generally indicated at 32 which is positioned at the bottom (or outlet end) of the apparatus, shown in detail in FIG. 4. The track drive may include a pair of electrically driven controlled speed drive belts 34 and 36. Other arrangements for pulling the tubing through the apparatus will be apparent to those familiar with this art.

As shown in FIG. 1, the reel 30 and the supply of tubing 18 it carries are maintained within a sealed environment by means of a bell jar or the like 38 which seals against an upper plate 40. Likewise, the treated tubing which is collected at the bottom of the apparatus is contained within a sealed environment provided by bell jar arrangement 42 which seals against bottom plate 44, as depicted in FIG. 4. Other means for providing sealed chamber arrangements will be readily apparent to those familiar with this art.

The gas environment is provided by evacuating bell jars 38 and 42 by means of a vacuum pump connected to outlet arrangement (not shown). Because glass tube 69 (69') is in sealed communication with both 38 and 42 the entire system is evacuated in this manner. Other chamber designs may be used. The selected discharge gas, such as argon in this instance, is introduced to the system through inlet arrangement 41 to a pressure such as 0.6 Torr.

Because it is desirable to plasma discharge pre-treat the tubing 18 prior to a preferred apparatus has been described that includes three zones—a pre-treatment zone 60, a transition zone 82 and a monomer deposition zone 66 as are identified in FIG. 1.

Once a polymeric material has been treated in accordance with the invention, i.e., a surface of the polymeric material has a plasma deposited coating thereon, the polymeric material may be subsequently treated prior to administration to a patient. For example, therapeutic agents may be applied to the polymeric surface having a plasma deposited coating. Such therapeutic agents include anti-microbial agents, anti-fungal agents, anti-viral agents, anti-thrombogenic agents, and the like. While not wishing to be bound by any particular theory, it is believed that plasma deposition of certain monomers (e.g., N-vinyl-2-pyrrolidone) allows therapeutic agents to adsorb on the polymeric surface. Preferably, applying therapeutic agents to polymeric surfaces having plasma deposited coatings thereon is accomplished in situ, i.e., at or near the point of administration to a patient because of sterility concerns.

Inside Diameter Surface Treatment

In an alternative embodiment of the present invention, an inside diameter surface of the tubing can be treated so as to improve its lubricity. To achieve ID treatment, an additional glow discharge zone can be added to the apparatus shown in FIG. 1, wherein an ID treatment zone is preferably located after the inert gas plasma pre-treatment zone and prior to the monomer deposition zone.

Figure 6:
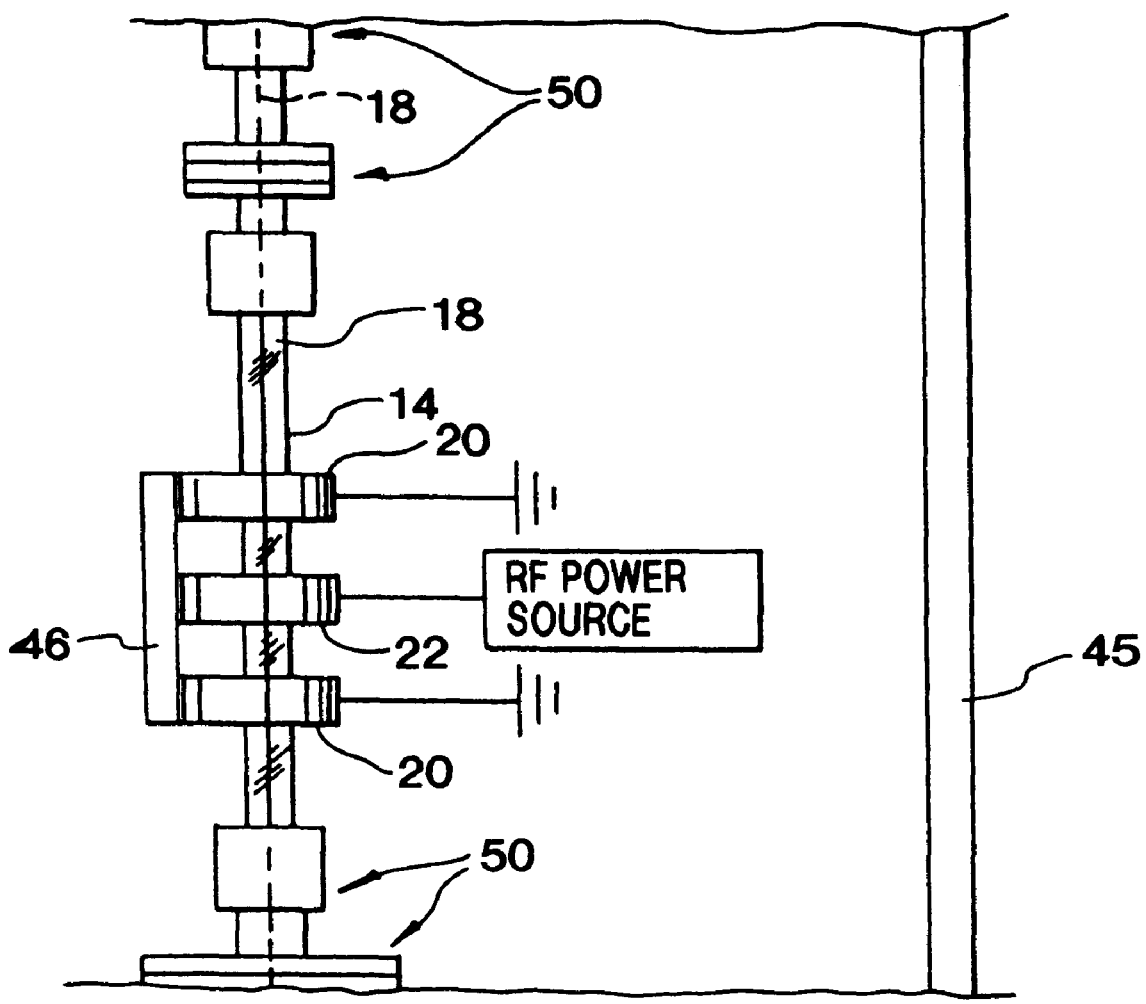
FIG. 6 is a showing of an apparatus according to the invention for plasma discharge treating a coiled length of tubing preferentially on its ID.

Due to the permeability of silicone rubber, tubing 18 absorbs gas as it remains on reel 30 in bell 38, the gas equilibrating within the tubing 18 ID usually at least an hour or so to fill the tubing 18 so that, as the tubing 18 passes through capillary tube 14, it carries the discharge gas with it into the discharge zone between the electrodes, as shown in FIG. 6. If using tubing other than silicone, such other tubing not being as readily permeable, a standing time of several additional hours allows the atmosphere of the chamber to permeate and/or to enter the tubing through its ends and equilibrate. Upon establishment of pulsed RF power such as that described with reference to FIG. 1, preferential discharge occurs within tubing 18 between the electrodes as the tubing passes from reel 30 to bell 42 for collection. In this manner surface modification of the slip characteristics of the ID of tubing 18 is effected, whether merely by hardening or by coating, as desired and depending on the type of gas used.

As shown in FIG. 6, inside the electrodes 20 and 22 is a section of glass capillary 14 serving as a reactor, the capillary 14 having an inside diameter that is close fitting relative to the OD of the polymeric tubing, i.e., the inner surface of the glass capillary 14 is close enough to the OD surface of the polymeric tubing such that the glow discharge preferentially occurs on the ID surface of the tubing. For example, approximately 2 to 7% (about 5–7% being most preferred) greater than the outside diameter of the tubing 18 which is being treated is typically required in order for the glow to be preferentially produced inside of the silicone tubing. When a space of greater than about 0.006 inch or about 7% exists between the tubing 18 and the capillary 14, undesired discharge may occur in the space around the outside of the tubing 18 and within the capillary 14 rather than preferentially inside of the tubing 18 only.

It can be seen from the foregoing description that the invention in its most preferred form presently comprises a plasma reactor and method which produces a glow discharge within the lumen of small diameter silicone tubing for the purpose cross-linking and hardening the inner surface. This treatment can be performed continuously meaning that tubing is fed from a spool of 1000+ feet of tubing and treated as it moves through an outer glow discharge zone and then an inner glow discharge zone of the reactor then it passes into a receiving chamber. Various electrode configurations may be used but they all provide the best performance when pulsed RF power is used in treating the ID surface of polymeric tubing. Magnetic fields can be used to enhance the discharges and allow lower pressure operation and treatment of multi-lumen tubing.

Preferably, accomplishing a preferential glow discharge on the ID surface of polymeric tubing is done by reactance coupling that utilizes power provided by a pulsed radio frequency power source. More preferably, the pulsed radio frequency power source provides a continuous sequence of "on" periods and "off" periods, where the "on" periods having a duration of about 1 to about 10 milliseconds and the "off" periods have a duration of about 4 to about 800 milliseconds.

As described above, glow discharge treatments of both inside and outside of the tubing described above may involve the use of "inert" gases. Gas pressure in the ID surface treatment zone is preferably maintained at a relatively higher pressure than the pre-treatment zone. This fills the tubing with inert gas to a stable pressure while the pre-treatment zone is maintained at a relatively lower pressure which is more desirable for the outer surface plasma treatment. These differential pressures are maintained by using gas flow controls, orifices, and automatic exhaust valve pressure controllers as will be known by those familiar with this art.

In a variation on the above treatment, a polymerizable siloxane vapor, or other polymerizable gas e.g., silane or fluorocarbon may be introduced into the ID surface treatment zone. The vapors permeate the tubing wall and, upon passing through the ID treatment zone, become polymerized as a coating inside of the tubing. This means that it is also possible to deposit plasma polymers inside of silicone tubing without feeding the vapors through the end of the tube which would be impractical in long, small diameter tubing.

The possible uses of this invention include any tubular device which has a moving part in contact with the ID of silicone rubber tubing or any polymer which exhibits a tacky surface, particularly those devices in which the contact occurs within the lumen of silicone tubing.

One advantage of treated tubing is the improved "stringability" it offers for inserting wire torsion coils, guide wire, braided wire and the like into the tubing through the lumen thereof. This is an important advantage in cases such as pacing leads for example where small wires must be threaded or pushed through the lumen over distances of two to four feet, typically.

Heretofore, "stringability" has been accomplished by treating the tubing with an agent such as FREON or hydrocarbons, such as heptane and the like, to swell it and using isopropyl alcohol to wet the wire and lumen while pushing the wire into the lumen. All of this is now obviated by the fact that tubing treated according to this invention will readily accept insertion of a wire or the like without any other treatment step by merely pushing the wire into the lumen. This is due to the increased and improved slip characteristics imparted to the tubing by the treatment of this invention.

Figure 7:
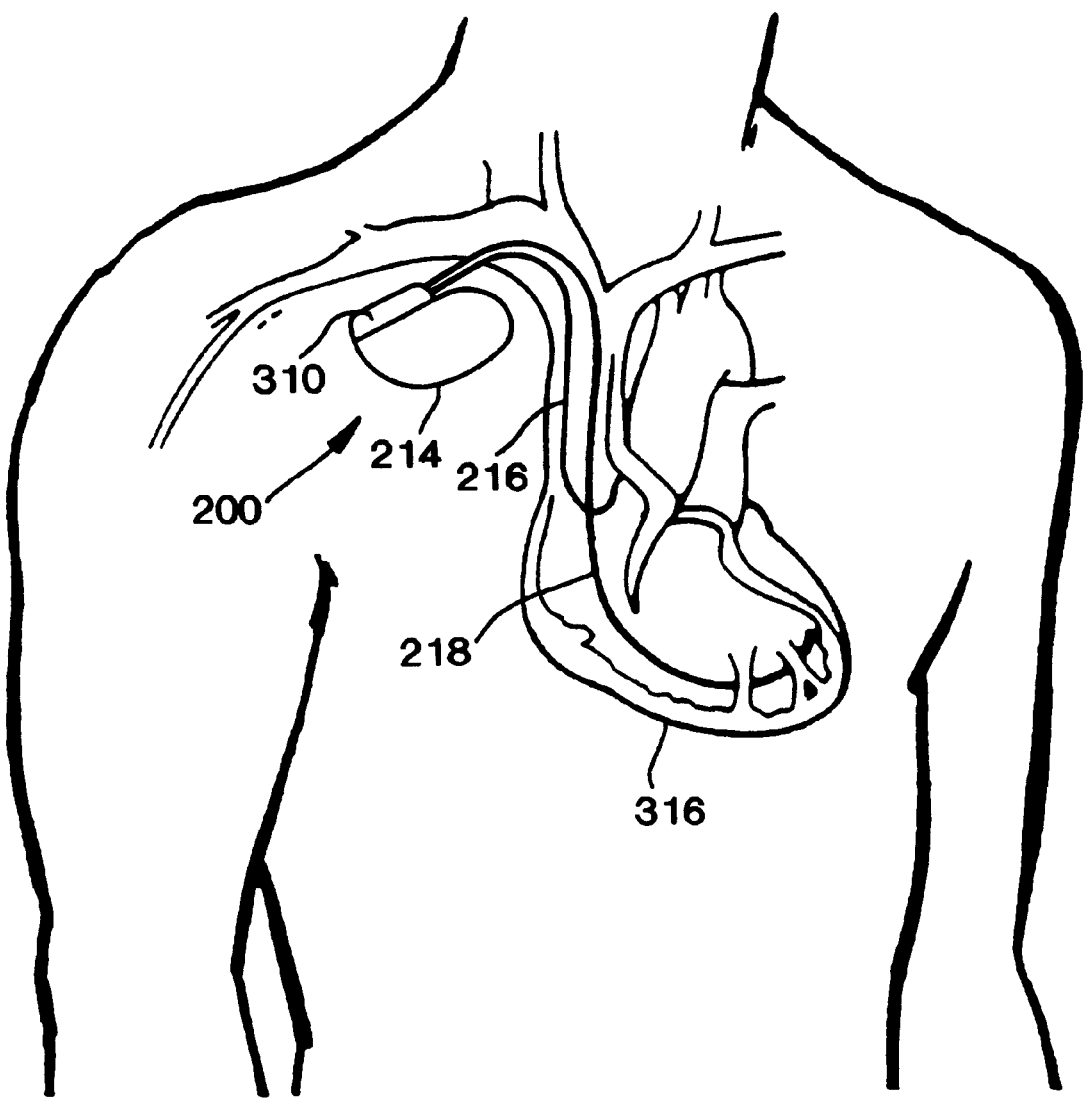
FIG. 7 is a simplified schematic of an implantable medical device in accordance with the invention.

FIG. 7 is a simplified schematic view of an implantable medical device 200 embodying the present invention, where at least one improved pacing and sensing lead 218 or 288 is attached to an hermetically sealed enclosure 214 and implanted near human heart 316. In the case where implanted medical device 200 is a pacemaker it includes at least one or both of pacing and sensing leads 216 and 218. Pacing and sensing leads 216 and 218 sense electrical signals attendant to the depolarization and re-polarization of the heart 316, and provide pacing pulses for causing depolarization of cardiac tissue in the vicinity of the distal ends thereof. Implantable medical device 200 may be an implantable cardiac pacemaker such as those disclosed in U.S. Pat. No. 5,158,078 to Bennett et al, U.S. Pat. No. 5,312,453 to Shelton et al, or U.S. Pat. No. 5,144,949 to Olson, all hereby incorporated herein by reference in their respective entireties.

Implantable medical device 200 may also be a PCD (Pacemaker-Cardioverter-Defibrillator) corresponding to any of the various commercially available implantable PCDs, with the substitution of pacing or sensing leads connector module 212 of the present invention for the connector block assembly otherwise present. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless or U.S. Pat. No. 4,821,723 to Baker et al., all hereby incorporated herein by reference in their respective entireties. Those devices may be employed directly in conjunction with the present invention, and most preferably are practiced such that the feedthroughs interconnecting the circuitry therein to their connector blocks is located to permit ready access between the feedthroughs and the electrical connectors disposed within the connector bores of connector or header module 212.

Alternatively, implantable medical device 200 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device for use in conjunction with electrical leads, and is believed to be particularly advantageous in those contexts where multiple medical electrical leads are employed and desired.

In general, hermetically sealed enclosure 214 includes an electrochemical cell such as a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a micro-computer based system with A/D conversion of sampled EGM amplitude values. The particular electronic features and operations of the implantable medical device are not believed to be of overriding significance in respect of practicing the present invention. One exemplary operating system is described in commonly assigned, co-pending U.S. patent application Ser. No. 08/678,219, filed Jul. 11, 1996, for "Minimally Invasive Implantable Device for Monitoring Physiologic Events," the disclosure of which is hereby incorporated by reference herein in its entirety.

It is to be understood that the present invention is not limited in scope to either single-sensor or dual-sensor pacemakers, and that other sensors besides activity and pressure sensors could be used in practicing the present invention. Nor is the present invention limited in scope to single-chamber pacemakers. The present invention may also be practiced in connection with multiple-chamber (e.g., dual-chamber) pacemakers.

Figure 8:
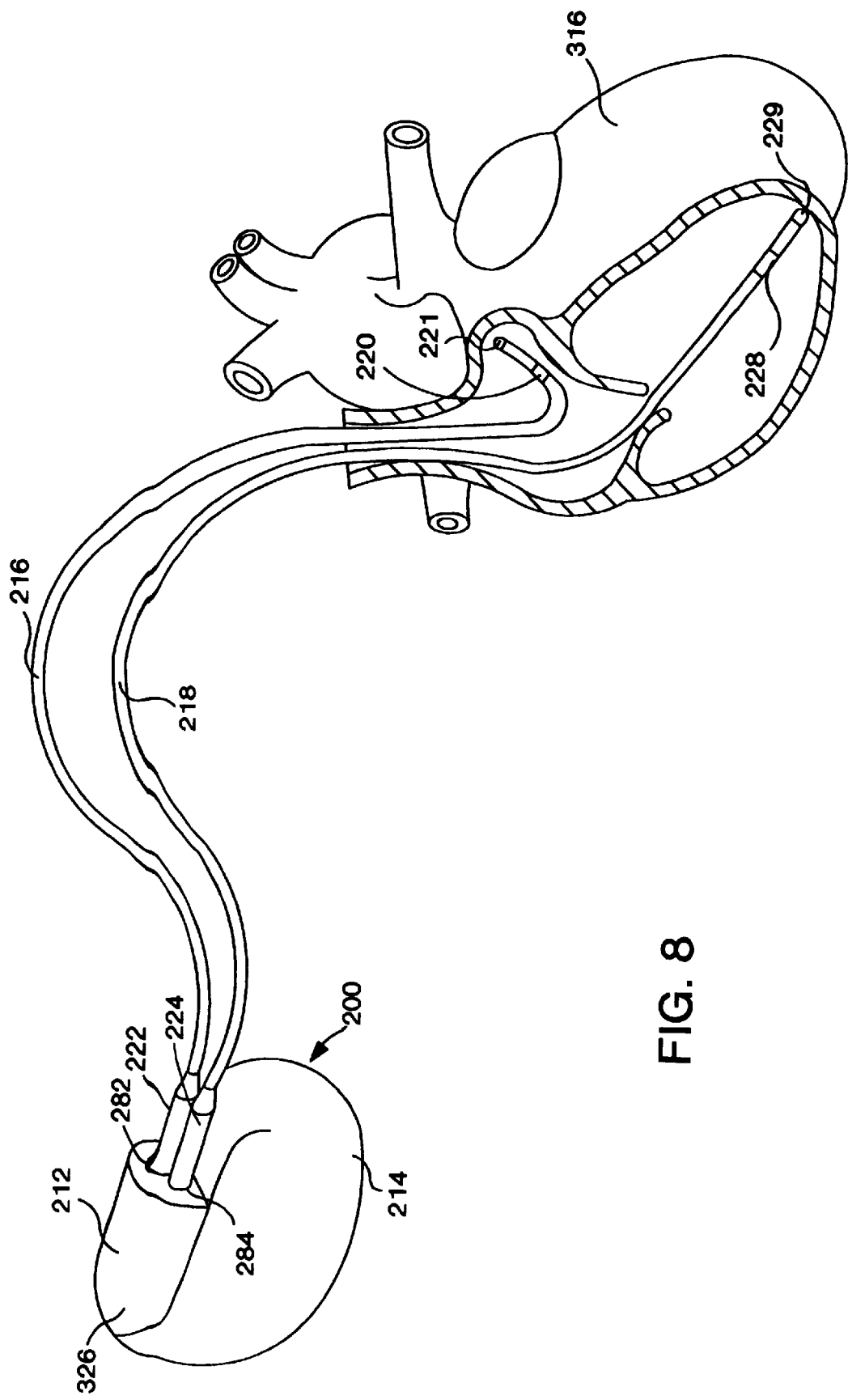
FIG. 8 is a simplified schematic of an implantable medical device in accordance with the invention as it relates to a patient's heart.

FIG. 8 depicts connector module 212 and hermetically sealed enclosure 214 of implantable medical device or dual chamber pacemaker IPG 200 as they relate to a patient's heart 316. Atrial and ventricular pacing leads 216 and 218 extend from connector header module 212 to the right atrium and ventricle, repsectively. Atrial electrodes 220 and 221 disposed at the distal end of the atrial pacing lead 216 are located in the right atrium. Ventricular electrodes 228 and 229 at the distal end of ventricular pacing lead 218 are located in the right ventricle.

Figure 9:
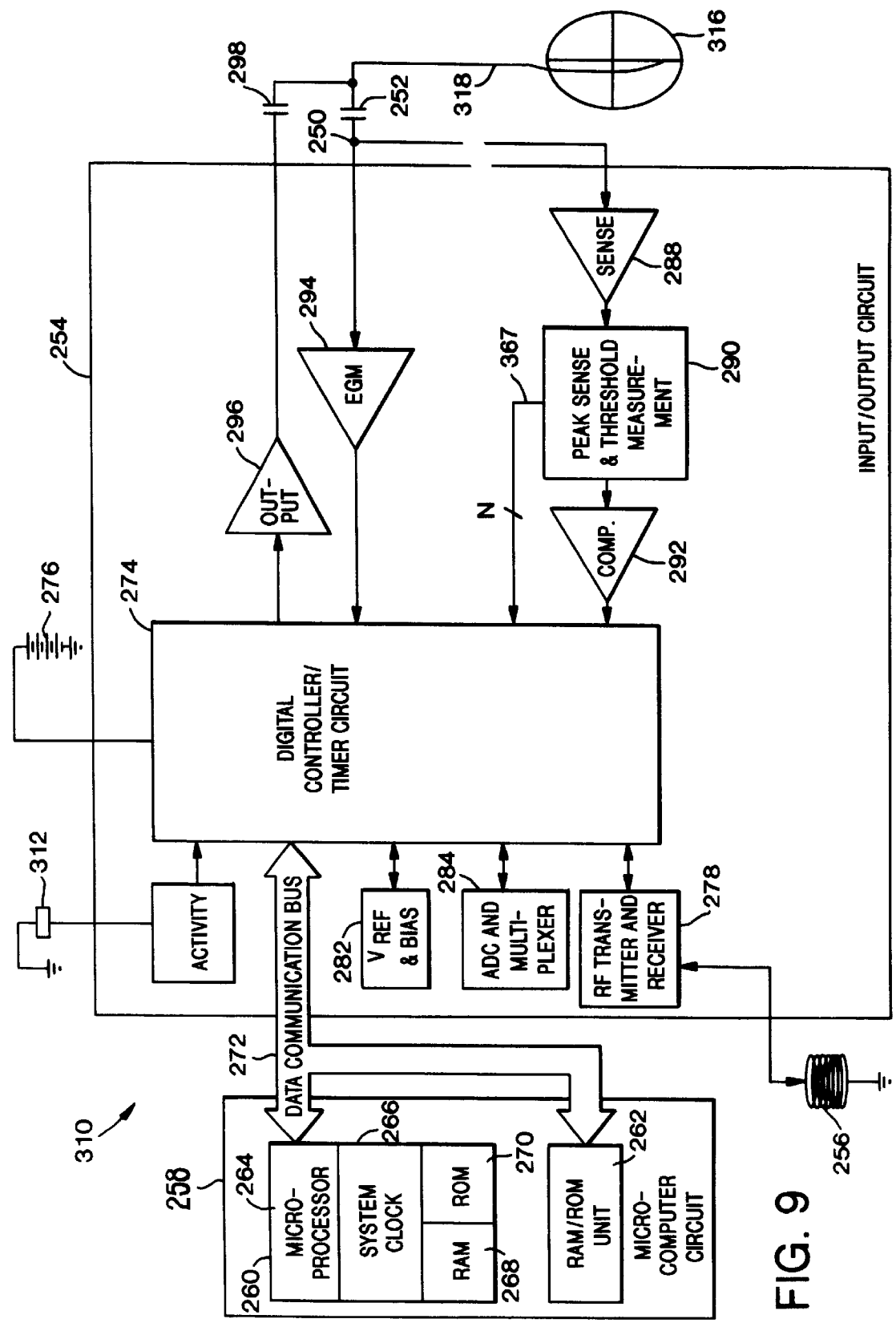
FIG. 9 is a block diagram illustrating constituent components of one embodiment in accordance with the invention.

FIG. 9 shows a block diagram illustrating the constituent components of a pacemaker 310 in accordance with one embodiment of the present invention, where pacemaker 310 has a microprocessor-based architecture. The present invention may be utilized in conjunction with other implantable medical devices, however, such as cardioverters, defibrillators, cardiac assist systems, and the like, or in conjunction with other design architectures.

In the illustrative embodiment shown in FIG. 9, pacemaker 310 includes an activity sensor 312, which is preferably a piezoceramic accelerometer bonded to the hybrid circuit inside the pacemaker housing. Piezoceramic accelerometer sensor 312 provides a sensor output which varies as a function of a measured parameter that relates to the metabolic requirements of patient.

Pacemaker 310 of FIG. 9 is most preferably programmable by means of an external programming unit (not shown in the Figures). One such programmer suitable for the purposes of the present invention is the commercially available Medtronic Model 9790 programmer. The programmer is a microprocessor device which provides a series of encoded signals to pacemaker 310 by means of a programming head which transmits radio-frequency (RF) encoded signals to pacemaker 310 according to a telemetry system such as that described in U.S. Pat. No. 5,312,453 to Wyborny et al., the disclosure of which is hereby incorporated by reference herein in its entirety. It is to be understood, however, that the programming methodology disclosed in Wyborny et al. patent is identified herein for the illustrative purposes only, and that any programming methodology may be employed so long as the desired information is transmitted to and from the pacemaker. One of skill in the art may choose from any of a number of available programming techniques to accomplish this task.

Pacemaker 310 is schematically shown in FIG. 9 to be electrically coupled to a pacing lead 318 disposed in patient's heart 316. Lead 318 preferably includes an intracardiac electrode disposed at or near its distal end and positioned within the right ventricular (RV) or right atrial (RA) chamber of heart 316. Lead 318 may have unipolar or bipolar electrodes disposed thereon, as is well known in the art. Although an application of the present invention in the context of a single-chamber pacemaker is disclosed herein for illustrative purposes, it is to be understood that the present invention may equally well be applied in the context of a dual-chamber pacemakers or other implantable device.

Lead 318 is coupled to a node 250 in the circuitry of pacemaker 310 through input capacitor 252. In the presently disclosed embodiment, accelerometer 312 is attached to the hybrid circuit inside pacemaker 310, and is not shown explicitly in FIG. 9. The output from accelerometer 312 is coupled to input/output circuit 254. Input/output circuit 254 contains analog circuits for interfacing to heart 316, accelerometer 312, antenna 256, and circuits for the application of stimulating pulses to heart 316 to control its rate under control of software-implemented algorithms in microcomputer circuit 258.

Microcomputer circuit 258 preferably comprises on-board circuit 260 and off-board circuit 262. Circuit 258 may correspond to the microcomputer circuit disclosed in U.S. Pat. No. 5,312,453 to Shelton et al. the disclosure of which is hereby incorporated by reference herein in its entirety. On-board circuit 260 includes microprocessor 264, system clock circuit 266, and on-board RAM 268 and ROM 270. In the presently disclosed embodiment of the invention, off-board circuit 262 comprises a RAM/ROM unit. On-board circuit 260 and off-board circuit 262 are each coupled by a data communication bus 272 to a digital controller/timer circuit 274. Microcomputer circuit 258 may form a custom integrated circuit device augmented by standard RAM/ROM components.

The electrical components shown in FIG. 9 are powered by an appropriate implantable battery power source 276, in accordance with common practice in the art. For the sake of clarity, the coupling of battery power to the various components of pacemaker 310 is not shown in the Figures.

Antenna 256 is connected to input/output circuit 254 to permit uplink/downlink telemetry through RF transmitter and receiver unit 278. Unit 278 may correspond to the telemetry and program logic disclosed in U.S. Pat. No. 4,566,063 issued to Thompson et al., hereby incorporated by reference herein in its entirety, or to that disclosed in the above-referenced Wyborny et al. patent. The particular programming and telemetry scheme chosen is not believed to be critical for purposes of practicing the present invention so long as entry and storage of values of rate-response parameters are permitted.

$V_{REF}$ and Bias circuit 282 generates a stable voltage reference and bias currents for the analog circuits of input/output circuit 254. Analog-to-digital converter (ADC) and multiplexer unit 284 digitizes analog signals and voltages to provide "real-time" telemetry intracardiac signals and battery end-of-life (EOL) replacement function.

Operating commands for controlling the timing of pacemaker 310 are coupled by data bus 272 to digital controller/timer circuit 274, where digital timers and counters establish the overall escape interval of the pacemaker as well as various refractory, blanking and other timing windows for controlling the operation of the peripheral components disposed within input/output circuit 254.

Digital controller/timer circuit 274 is preferably coupled to sensing circuitry, including sense amplifier 288, peak sense and threshold measurement unit 290 and comparator/threshold detector 292. Circuit 274 is further preferably coupled to electrogram (EGM) amplifier 294 for receiving amplified and processed signals sensed by an electrode disposed on lead 318. Sense amplifier 288 amplifies sensed electrical cardiac signals and provides an amplified signal to peak sense and threshold measurement circuitry 290, which in turn provides an indication of peak sensed voltages and measured sense amplifier threshold voltages on multiple conductor signal path 367 to digital controller/timer circuit 274. An amplified sense amplifier signal is then provided to comparator/threshold detector 292. Sense amplifier 288 may correspond to that disclosed in U.S. Pat. No. 4,379,459 to Stein, which is hereby incorporated by reference herein in its entirety.

The electrogram signal provided by EGM amplifier 294 is employed when the implanted device is being interrogated by an external programmer (not shown) to transmit by uplink telemetric means a representation of an analog electrogram of the patient's electrical heart activity. See, for example, U.S. Pat. No. 4,556,063 to Thompson et al., hereby incorporated by reference herein in its entirety. Output pulse generator 296 provides pacing stimuli to patient's heart 316 through coupling capacitor 298 in response to a pacing trigger signal provided by digital controller/timer circuit 274 each time the escape interval times out, an externally transmitted pacing command is received, or in response to other stored commands as is well known in the pacing art. Output amplifier 296 may correspond generally to the output amplifier disclosed in U.S. Pat. No. 4,476,868 to Thompson, also incorporated by reference herein in its entirety.

While specific embodiments of input amplifier 288, output amplifier 296 and EGM amplifier 294 have been identified herein, this is done for the purposes of illustration only. The specific embodiments of such circuits are not critical to practicing the present invention so long as the circuits provide means for generating a stimulating pulse and are capable of providing digital controller/timer circuit 274 with signals indicative of natural or stimulated contractions of the heart.

EXAMPLES

While polymeric surface treatment methods and apparatuses in accordance with the invention have been described herein, the following non-limiting examples will further illustrate the invention.

Conventional silicone tubing (0.5 inch outer diameter, available from Cole-Parmer Inc., Vernon Hills, Ill.) was loaded in an upper chamber, shown as 38, of an apparatus as shown in FIG. 1, described above. The upper chamber was evacuated. Argon gas flow was started at 1 sccm into the upper chamber. The parameters set for a throttle valve for the upper chamber and a constant RF (radio frequency) power in the plasma pre-treatment zone are shown in Table 2, below. An argon discharge began in the plasma pre-treatment zone.

The monomer used was N,vinyl-2-pyrrolidone (NVP) (99.5% optical grade, redistilled, available from Polysciences, Inc., Warrington, Pa.) and was placed in the monomer reservoir, shown as 52 in FIG. 4. The temperatures of the monomer source (including the reservoir and the conduit), RF power level, pulse width used are indicated in Table 2, below.

TABLE 2

| Condition | Example 1 | Example 2 | Example 3 | Example 4 |
| --- | --- | --- | --- | --- |
| Throttle valve setting (pre-treat. zone) | 400 mT | 400 mT | 400 mT | 400 mT |
| Power level (Pre-treat. zone) | 20 watts | 40 watts | 40 watts | 40 watts |
| Monomer temp. (reservoir/conduit) | 51° C. | 51° C. | 51° C. | 51° C. |
| Throttle valve setting (monomer deposition zone) | 500 mT | 500 mT | 500 mT | 500 mT |
| Power level (monomer deposition zone) | 8 watts/ 0 watts | 8 watts/ 0 watts | 4 watts/ 0 watts | 8 watts/ 0 watts |
| Power Pulse width (monomer deposition zone) | 4 milliseconds | 4 milliseconds | 4 milliseconds | 4 milliseconds |
| Duty Cycle | 20% | 20% | 20% | 20% |
| Line Speed | 3.2 inches/min. | 3.2 inches/min. | 3.2 inches/min. | 8.8 inches/min. |

A bluish colored glow discharge was observed in the deposition zone when the NVP flow started. The monomer deposition zone was run in this manner for 20 minutes so that about 5 feet of tubing had monomer deposited on the outer surface.

Tubing from Examples 1–4 were then soaked for 24 hours in deionized water and then evaluated for % retention of the monomer based on FTIR analysis. Each of the treated tubing examples was analyzed using fourrier transform infra-red (FTIR) spectroscopy to detect plasma deposited NVP coatings on the polymeric surface. A BIORAD FTS-175 spectrometer equipped with a UMA500 infrared microscope was used to obtain micro-attenuated total reflectance (ATR) spectra of the examples immediately following plasma deposition and after the same tubing segments of the examples were soaked in deionized water for 24 hours at room temperature, and then dried. Infrared absorbance peak intensities for 1680 $cm^{-1}$ (carbonyl absorbance from NVP) and 1015 $cm^{-1}$ (Si—O— absorbance from silicone tubing) were recorded as shown in Table 3.

Figure 10:
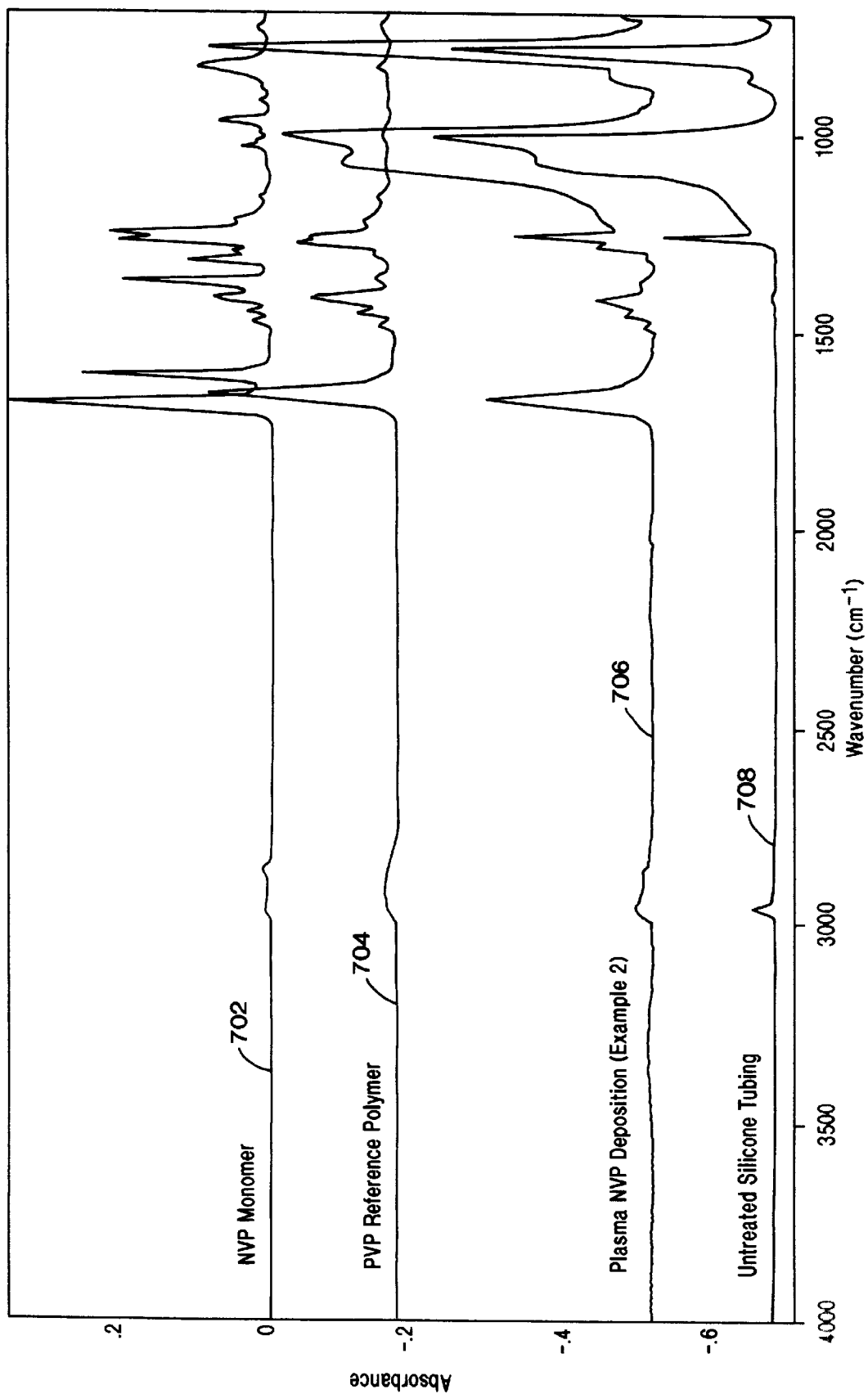
FIG. 10 is an overlay FTIR spectrum of silicone tubing treated in accordance with the invention.

FIG. 10 is an overlay FTIR spectrum of silicone tubing treated in accordance with the invention from Example 2 after soaking in deionized water for 24 hours (reference numeral 706). Comparative samples were also analyzed and appear on the overlay: NVP monomer alone (reference numeral 702), PVP polymer alone (reference numeral 704) and untreated silicone tubing (reference numeral 708).

The data in Table 3 shows the FTIR results from Examples 1–4, both before and after soaking 24 hours in deionized water.

TABLE 3

| Example | 1680 $cm^{-1}$ | 1015 $cm^{-1}$ | 1680 $cm^{-1}$/ 1015 $cm^{-1}$ |
| --- | --- | --- | --- |
| 1 - pre-soak | 0.04149 | 0.09752 | 0.4255 |
| 1 - post-soak | 0.002 | 0.45068 | 0.0044 |
| 2 - pre-soak | 0.02064 | 0.0488 | 0.4230 |
| 2 - post-soak | 0.00556 | 0.13019 | 0.0427 |
| 3 - pre-soak | 0.02019 | 0.07735 | 0.2610 |
| 3 - post-soak | 0.0025 | 0.19178 | 0.0130 |
| 4 - pre-soak | 0.02359 | 0.1862 | 0.1267 |
| 4 - post-soak | 0.002 | 0.24798 | 0.0081 |

Figure 11:
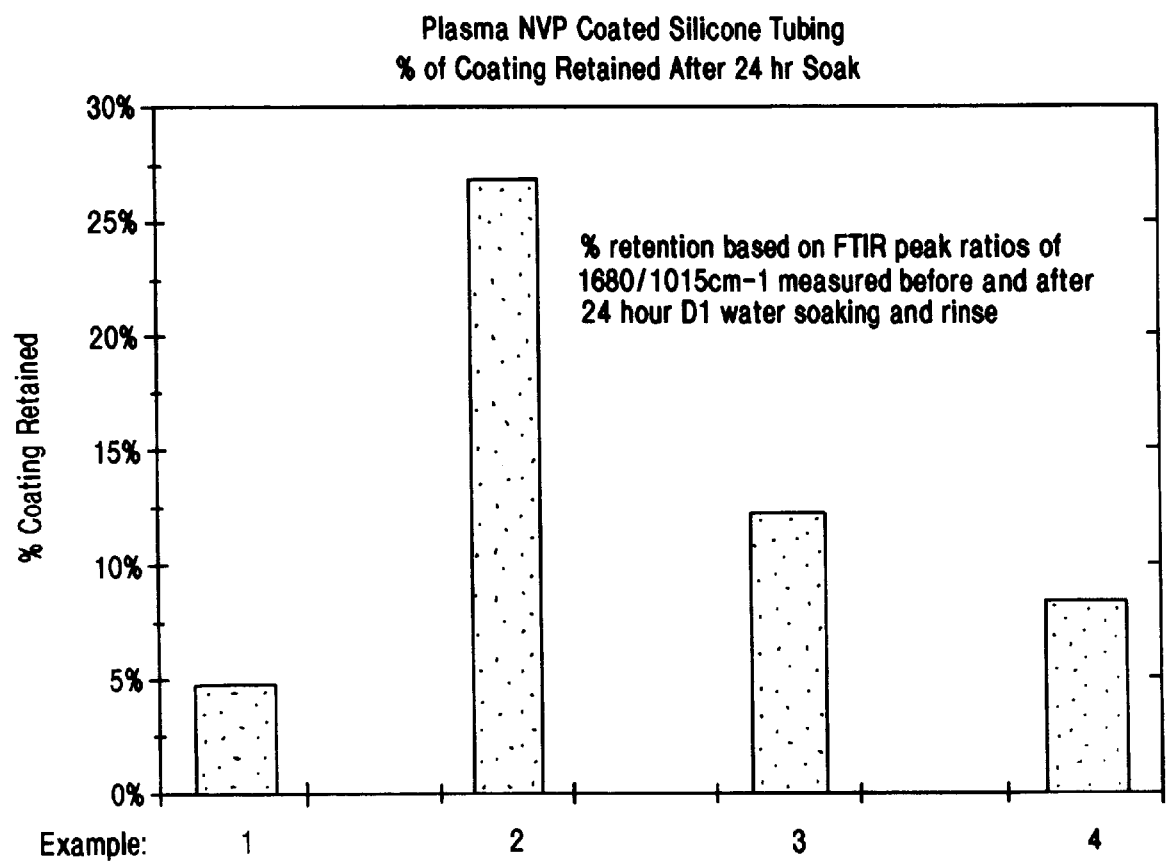
FIG. 11 is a graphic representation of monomer retention percents of tubing treated in accordance with the invention.

The results shown in FIG. 10 were calculated based on the relative infrared absorbance peak values at 1680 $cm^{-1}$ divided by the peak values at 1015 cm$^{-1}$ which indicates the relative quantity of ppNVP (plasma polymerized NVP) on the surface of each tubing before and after soaking, as shown by the data in Table 3. Example 2 retained over 25% of its FTIR intensity after soaking and rinsing in deionized water (see, FIG. 10 for spectrum). Examples 1, 3 and 4 were in the 5–12% range (see, FIG. 11 for retention percentages after soaking).

It is believed that the pre-soak absorbance values for the 1680 cm$^{-1}$ NVP absorbance were artificially high due to the presence of residual monomer vapors within the ppNVP-silicone tubing matrix immediately following plasma deposition. Soaking of the tubing in deionized water for 24 hours was done to remove this residual monomer and any of the plasma deposited coating that may have been soluble and not attached to the silicone surface.

The tubing from Examples 1–4 were then evaluated in a Friction Test using a modified "Coefficient of Friction of Plastic Film and Sheeting" (Sled Test, ASTM 1894-78). A slip/peel tester (Instrumentors SP-102B Slip/Peel Tester) provided a moving platen with speed control and load cell. A custom bed, which was attached to the platen, held the samples of tubing. A sled with a polished stainless steel bottom was dragged over the samples of the tubing. The test set-up was as follows: variable bed speed of 5 inches/minute; data collection using a data acquisition board; and load cells. The test procedure involved setting the bed speed to 6 inches/min.; the outer surface of the tubing samples were wiped with water and mounted to the bed; the sled was wiped with acetone and placed on the samples and the force data acquired with the data acquisition board. The data collected represented the force or horizontal load required to displace the weighted sled. Two modifications were made to this test to allow for "wet" testing. First, the tubing bed was placed in a shallow pan which was filled with deionized water for testing. Steel rods were inserted inside of the tubing samples to prevent them from floating in the filled pan.

Figure 12:
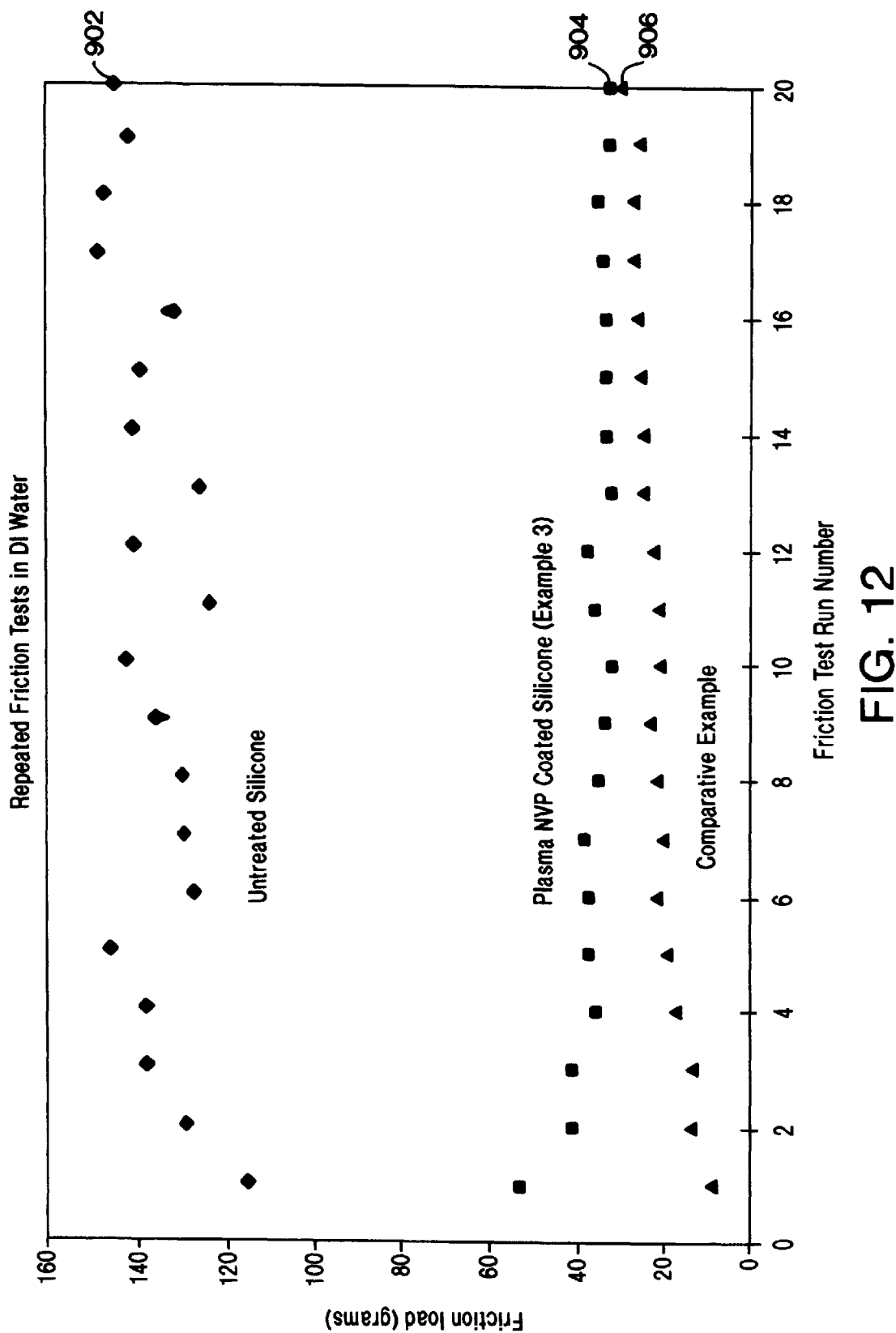
FIG. 12 is a graphic representation of repeated friction tests performed in an aqueous environment with tubing treated in accordance with the invention.

FIG. 12 is a graphic representation of repeated friction tests performed in an aqueous environment with tubing treated in accordance with the invention. Comparative examples of untreated silicone tubing (reference numeral 902) and a commercially available surface modified tubing (BIOCOAT on polyurethane, available from Biocoat Incorporated, Fort Washington, Pa.) were also run with a sample of silicone tubing treated as in Example 3 above (reference numeral 904). The friction test performed in a shallow pan of water, as described above, was repeated with the same tubing samples 20 times. As can be seen, both the plasma NVP coated Example 3 and the BIOCOAT sample provide much lower friction than untreated silicone tubing immediately following immersion in water. However, the plasma NVP sample maintained its low friction surface through the course of 20 repeated pull tests, while the BIOCOAT sample gradually increased in friction over the 20 pulls. This suggests that the plasma NVP surface is likely more stable and relatively better adhered than the comparative BIOCOAT surface.

Figure 13:
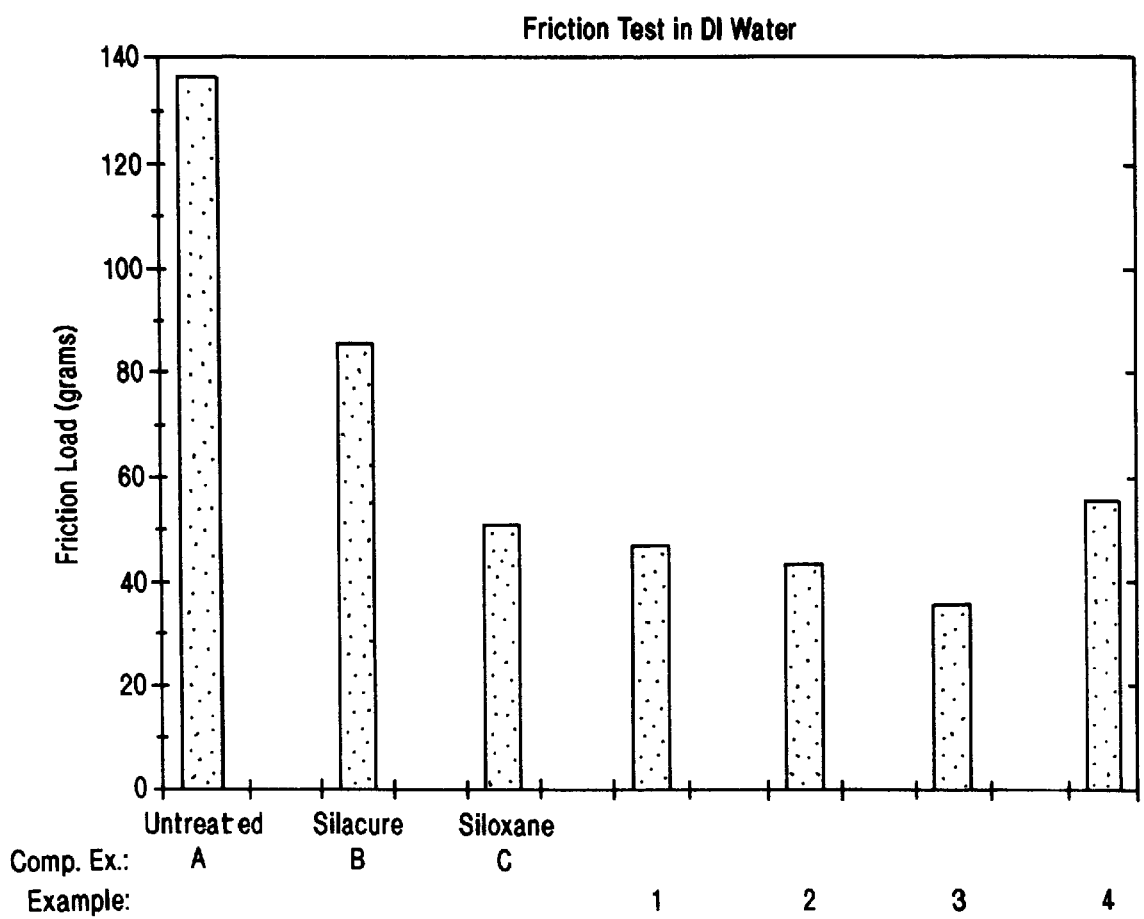
FIG. 13 is a graphic representation of friction tests performed in an aqueous environment with tubing treated in accordance with the invention.

FIG. 13 is a graphic representation of friction tests performed in an aqueous environment with tubing treated in accordance with the invention, as in Examples 1–4 above. Comparative examples were also evaluated. Comparative example A was untreated silicone tubing, Comparative example B was inert gas plasma treated tubing, and Comparative example C was plasma deposited siloxane on silicone tubing. The data indicates that inert gas plasma reduces friction by approximately one third while the siloxane and plasma NVP depositions reduce friction to less than about half, as compared to untreated silicone.

The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached thereto.

What is claimed is:

1. A polymeric tubing comprising:
   a tubing wall having an outer diameter surface and an inner diameter surface forming at least one lumen therein, wherein the outer diameter surface comprises a surface treated by exposure to a plasma glow discharge in the presence of an inert gas and deposition of a monomer for a time sufficient to modify the slip characteristics of the outer diameter surface.

2. The tubing of claim 1 wherein exposure to a plasma glow discharge comprises exposing the outer diameter surface to the plasma glow discharge for a time sufficient to reduce the coefficient of sliding friction of the treated outer diameter surface by at least 70%.

3. The tubing of claim 1 wherein exposure to a plasma glow discharge comprises exposing the outer diameter surface to the plasma glow discharge for a time sufficient to reduce the coefficient of sliding friction of the treated outer diameter surface as measured after a 24 hour exposure to an aqueous environment.

4. The polymeric tubing of claim 1 wherein exposure to a plasma glow discharge comprises exposing a silicone tubing wall to the plasma glow discharge.

5. The polymeric tubing of claim 1 wherein deposition of the monomer comprises deposition of N-vinyl-2-pyrrolidone.

6. The polymeric tubing of claim 1 wherein the outer diameter surface comprises a surface to which a therapeutic agent is applied, after exposure to a plasma glow discharge.

* * * * *